United States Patent [19]

Gaster et al.

[11] Patent Number: 5,705,498
[45] Date of Patent: Jan. 6, 1998

[54] PIPERIDINE DERIVATIVES AS 5-HT$_4$ RECEPTOR ANTAGONISTS

[75] Inventors: Laramie Mary Gaster, Bishop's Stortford; Paul Adrian Wyman, Epping, both of England

[73] Assignee: SmithKline Beecham plc., Brentford, England

[21] Appl. No.: 433,369

[22] PCT Filed: Nov. 2, 1993

[86] PCT No.: PCT/EP93/03054

§ 371 Date: May 4, 1995

§ 102(e) Date: May 4, 1995

[87] PCT Pub. No.: WO94/10174

PCT Pub. Date: May 11, 1994

[30] Foreign Application Priority Data

Nov. 5, 1992 [GB] United Kingdom ............... 9223155
May 11, 1993 [GB] United Kingdom ............... 9309644
Jul. 22, 1993 [GB] United Kingdom ............... 9315202

[51] Int. Cl.$^6$ .............. C07D 213/80; C07D 401/12; C07D 498/04; A61K 31/395
[52] U.S. Cl. .............. 514/214; 514/224.5; 514/366; 514/375; 514/393; 514/411; 540/547; 540/558; 540/586; 544/32; 544/89; 544/252; 546/94; 548/217; 548/150; 548/302.4; 548/428
[58] Field of Search ............... 548/217, 150, 548/302.4, 428; 546/94; 544/32, 89, 252; 540/547, 558, 586; 514/214, 224.5, 366, 375, 393, 411

[56] References Cited

FOREIGN PATENT DOCUMENTS

| | | |
|---|---|---|
| 0 407 137 A3 | 1/1991 | European Pat. Off. . |
| 0 501 322 A1 | 9/1992 | European Pat. Off. . |
| 2 176 785 | 1/1987 | United Kingdom . |
| WO93/03725 | 3/1993 | WIPO . |
| WO93/05038 | 3/1993 | WIPO . |
| WO93/18036 | 9/1993 | WIPO . |

OTHER PUBLICATIONS

Faye et al., Medicinal Chemistry 4th ed., Williams & Wilkins (1995), pp. 156–157.

*Primary Examiner*—Mukund J. Shah
*Assistant Examiner*—Bruck Kifle
*Attorney, Agent, or Firm*—Charles M. Kinzig; Edward T. Lentz

[57] ABSTRACT

Compounds of formula (I):

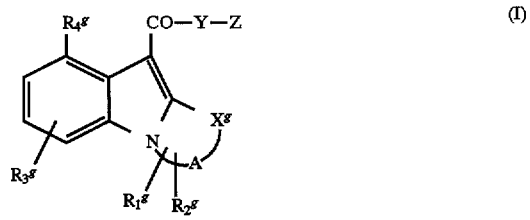

wherein $X^g$ is O, S, SO, SO$_2$, CH$_2$, CH, N or NR wherein R is hydrogen or C$_{1-6}$alkyl;

A is a saturated or unsaturated polymethylene chain of 2–4 carbon atoms;

$R_1^g$ and $R_2^g$ are hydrogen or C$_{1-6}$alkyl;

$R_3^g$ is hydrogen, halo, C$_{1-6}$alkyl, amino, nitro or C$_{1-6}$alkoxy;

$R_4^g$ is hydrogen, halo, C$_{1-6}$alkyl or C$_{1-6}$alkoxy,

Y is O or NH, or CO—Y together are a heterocyclic bioisostere;

Z is of sub-formula:

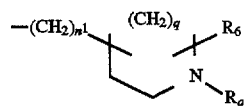

wherein —(CH$_2$)$_n^1$ is attached at carbon; and $n^1$ is 0, 1, 2, 3 or 4;

q is 0, 1, 2 or 3;

$R_a$ is a straight or branched chain alkylene of chain length 1–6 carbon atoms terminally substituted by $R_7$ wherein $R_7$ is 3 to 8 membered heterocyclyl, 5 or 6 membered monocyclic heteroaryl or 9 or 10 membered fused bicyclic heteroaryl linked through carbon, or $R_7$ is C$_{2-7}$alkoxycarbonyl or secondary or tertiary hydroxy substituted C$_{1-6}$alkyl; and $R_6$ is hydrogen or C$_{1-6}$alkyl;

are useful as 5HT$_4$ receptor antagonists.

21 Claims, No Drawings

PIPERIDINE DERIVATIVES AS 5-HT$_4$ RECEPTOR ANTAGONISTS

This invention relates to novel compounds having pharmacological activity, to a process for their preparation and to their use as pharmaceuticals.

European Journal of Pharmacology 146 (1988), 187–188, and Naunyn-Schmiedeberg's Arch. Pharmacol. (1989) 340:403–410, describe a non classical 5-hydroxytryptamine receptor, now designated the 5-HT$_4$ receptor, and that ICS 205–930, which is also a 5-HT$_3$ receptor antagonist, acts as an antagonist at this receptor.

WO 91/16045 (SmithKline and French Laboratories Limited) describes the use of cardiac 5-HT$_4$ receptor antagonism in the treatment of atrial arrhythmias and stroke.

EP-A-501322 (Glaxo Group Limited), WO 93/02677, WO 93/03725, WO 93/05038, WO 93/05040 and WO 93/18036 (SmithKline Beecham plc) describe compounds having 5-HT$_4$ receptor antagonist activity.

It has now been discovered that certain novel compounds also have 5-HT$_4$ receptor antagonist properties.

Accordingly, the present invention provides compounds of formula (I) and pharmaceutically acceptable salts thereof, and the use of a compound of formula (I) or a pharmaceutically acceptable salt thereof:

X—CO—Y—Z   (I)

wherein

X is a monocyclic or polycyclic aromatic group, such as a group of formula (a), (b), (c), (d), (e), (f) or (g):

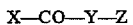

(a)

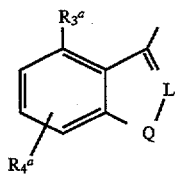

(b)

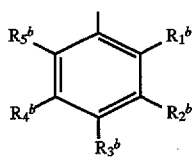

(c)

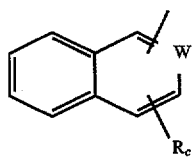

(d)

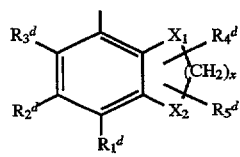

(e)

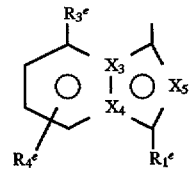

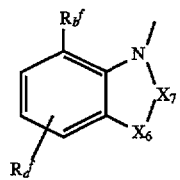

(f)

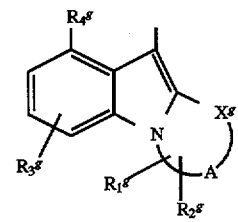

(g)

wherein

L is N or CR$_S$ wherein R$_S$ is hydrogen, C$_{1-6}$ alkoxy, halogen, C$_{1-4}$ alkyl or cyano;

Q is NR$_1^a$, CH$_2$, O or S;

W is CH or N;

in which X$_1$—(CH$_2$)$_x$—X$_2$ forms a 5-7 membered ring wherein X$_1$ is O or S; X$_2$ is O, S, NR or NRCO wherein R is hydrogen or C$_{1-6}$ alkyl; and x is 1, 2 or 3;

one of X$_3$ and X$_4$ is N and the other is C; and

X$_5$ is N or CR wherein R is hydrogen, C$_{1-6}$ alkoxy, halo, C$_{1-6}$ alkyl or cyano;

R$_1^a$ is hydrogen, C$_{1-10}$ alkyl, C$_{2-6}$ alkenyl, aralkyl, C$_{2-6}$ alkanoyl or C$_{2-6}$ alkanoyl C$_{1-3}$ alkyl;

R$_3^a$ is hydrogen, halo, C$_{1-6}$ alkyl, amino, nitro or C$_{1-6}$ alkoxy;

R$_4^a$ is hydrogen, halo, C$_{1-6}$ alkyl or C$_{1-6}$ alkoxy;

R$_1^b$ is C$_{1-6}$ alkoxy; and

R$_2^b$ is hydrogen, chloro or fluoro;

R$_3^b$ is hydrogen, C$_{1-6}$ alkyl, amino optionally substituted by a C$_{1-6}$ alkyl group, halo, hydroxy or C$_{1-6}$ alkoxy;

R$_4^b$ is hydrogen, halo, C$_{1-6}$alkyl, C$_{1-6}$ alkoxy, nitro, amino or C$_{1-6}$ alkylthio; and R$_5^b$ is hydrogen, halo, C$_{1-6}$ alkyl, C$_{1-6}$ alkoxy or amino;

R$_c$ is hydrogen, C$_{1-6}$ alkoxy, halo or C$_{1-6}$ alkyl;

R$_1^d$ is hydrogen, amino, halo, C$_{1-6}$ alkyl, hydroxy or C$_{1-6}$ alkoxy;

R$_2^d$ is hydrogen, halo, C$_{1-6}$ alkyl, C$_{1-6}$ alkoxy, nitro, amino or C$_{1-6}$ alkylthio;

R$_3^d$ is hydrogen, halo, C$_{1-6}$ alkyl, C$_{1-6}$ alkoxy or amino;

R$_4^d$ and R$_5^d$ are independently hydrogen or C$_{1-6}$ alkyl;

R$_1^e$ is hydrogen, halogen, CF$_3$, C$_{1-6}$ alkyl, C$_{1-6}$ alkoxy, C$_{1-6}$ alkylthio, C$_{1-6}$ alkylsulphonyl, C$_{1-6}$ alkylsulphinyl, C$_{1-7}$ acyl, cyano, C$_{1-6}$ alkoxycarbonyl, C$_{1-7}$ acylamino, hydroxy, nitro or amino, aminocarbonyl, or aminosulphonyl, optionally N-substituted by one or two groups selected from C$_{1-6}$ alkyl, C$_{3-8}$ cycloalkyl, and C$_{3-8}$ cycloalkyl C$_{1-4}$ alkyl or disubstituted by C$_4$ or C$_5$ polymethylene; phenyl or phenyl C$_{1-4}$ alkyl group optionally substituted in the phenyl ring by one or two of halogen, C$_{1-6}$ alkoxy or C$_{1-6}$ alkyl groups;

R$_3^e$ is hydrogen, halo, C$_{1-6}$ alkyl, amino, nitro or C$_{1-6}$ alkyl;

R$_4^e$ is hydrogen, halo, C$_{1-6}$ alkyl or C$_{1-6}$ alkoxy;

X$_6$-X$_7$ is NR$_z$—CO or CR$_1^f$R$_2^f$—CR$_3^f$R$_4^f$ where $R_z$ and $R_1{}^f$ to $R_4{}^f$ are independently hydrogen or $C_{1-6}$ alkyl; and/or $R_1{}^f/R_2{}^f$ and $R_3{}^f/R_4{}^f$ together are a bond and/or $R_1{}^f/R_2{}^f/R_3{}^f/R_4{}^f$ are joined to form $C_{3-6}$ polymethylene;

$R_a{}^f$ is hydrogen, halo, $C_{1-6}$ alkyl, amino, nitro or $C_{1-6}$ alkyl;

$R_b{}^f$ is hydrogen, halo, $C_{1-6}$ alkyl or $C_{1-6}$ alkoxy;

$X^g$ is O, S, SO, $SO_2$, $CH_2$, CH, N or NR wherein R is hydrogen or $C_{1-6}$ alkyl;

A is a saturated or unsaturated polymethylene chain of 2-4 carbon atoms;

$R_1{}^g$ and $R_2{}^g$ are hydrogen or $C_{1-6}$ alkyl;

$R_3{}^g$ is hydrogen, halo, $C_{1-6}$ alkyl, amino, nitro or $C_{1-6}$ alkoxy;

$R_4{}^g$ is hydrogen, halo, $C_{1-6}$ alkyl or $C_{1-6}$ alkoxy;

Y is O or NH;

Z is of sub-formula:

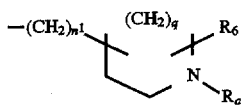

wherein

—$(CH_2)_n{}^1$ is attached at carbon; and $n^1$ is 0, 1, 2, 3 or 4;

q is 0, 1, 2 or 3;

$R_a$ is straight or branched chain alkylene of chain length 1–6 carbon atoms terminally substituted by $R_7$ wherein and $R_7$ is aryl, 3 to 8 membered cycloalkyl, 3 to 8 membered heterocyclyl, 5 or 6 membered monocyclic heteroaryl or 9 or 10 membered fused bicyclic heteroaryl linked through carbon, or $R_7$ is $C_{2-7}$ alkoxycarbonyl or secondary or tertiary hydroxy substituted $C_{1-6}$ alkyl; and $R_6$ is hydrogen or $C_{1-6}$ alkyl;

or a compound of formula (I) wherein the CO—Y linkage is replaced by a heterocyclic bioisostere;

in the manufacture of a medicament for use as a 5-$HT_4$ receptor antagonist.

Examples of alkyl or alkyl containing groups include $C_1$, $C_2$, $C_3$, $C_4$, $C_5$, $C_6$, $C_7$, $C_8$, $C_9$, $C_{10}$, $C_{11}$ or $C_{12}$ branched, straight chained or cyclic alkyl, as appropriate. $C_{1-4}$ alkyl groups include methyl, ethyl, n- and iso-propyl, n-, iso-, sec- and tert-butyl. Cyclic alkyl includes cyclopropyl, cyclobutyl, cyclopentyl, cyclohexyl, cycloheptyl and cyclooctyl optionally substituted by one or more alkyl groups of up to 4 carbon atoms.

Aryl includes phenyl and naphthyl optionally substituted by one or more substituents selected from halo, $C_{1-6}$ alkyl and $C_{1-6}$ alkoxy.

Halo includes fluoro, chloro, bromo and iodo, preferably chloro.

A suitable bioisostere for the amide or ester linkage containing Y in formula (I), is of formula:

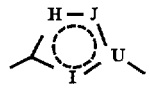

wherein the dotted circle represents one or two double bonds in any position in the 5-membered ring; H, J and I independently represent oxygen, sulphur, nitrogen or carbon, provided that at least one of H, J and I is other than carbon; U represents nitrogen or carbon.

Suitable examples of bioisosteres are as described for X, Y and Z in EP-A-328200 (Merck Sharp & Dohme Ltd.), such as an oxadiazole moiety.

L in formula (a) is favourably C—H, C—$CH_3$, C—Cl or C—$OCH_3$.

Q in formula (a) is favourably $NR_1{}^a$.

$R_1{}^a$ is preferably hydrogen or a methyl or ethyl group.

$R_1{}^b$ is preferably methoxy.

$R_3{}^b$ is preferably amino.

$R_4{}^b$ is preferably halo.

$R_5{}^b$ is preferably hydrogen.

A substituent when halo is selected from fluoro, chloro, bromo and iodo. $R_4{}^a$ when halo is preferably iodo.

Suitable examples of the $X_1$—$(CH_2)_x$—$X_2$ moiety include O—$(CH_2)_2$—O, O—$(CH_2)_3$—O, O—$CH_2$—O, O—$(CH_2)_2$—NR, O—$(CH_2)_2$—S or O—$CH_2$—CONR, wherein any of the methylene linkages are optionally mono- or di- substituted by $C_{1-6}$ alkyl groups, such as methyl. Preferably $X_1$—$(CH_2)_2$—$X_2$ is O—$(CH_2)_2$—O.

$R_1{}^d$ is preferably hydrogen or amino.

$R_2{}^d$ is preferably hydrogen or halo.

$R_3{}^d$ is preferably hydrogen or halo.

$R_4{}^d$ and $R_5{}^d$ are often hydrogen. When $R_4{}^d/R_5{}^d$ is $C_{1-6}$ alkyl, it is often methyl. In particular $R_4{}^d$ and $R_5{}^d$ are methyl such that the disubstituent containing $X_1$ and $X_2$ is O—C$(CH_3)_2$—O.

$R_1{}^e$ is preferably $CF_3$ or an ethyl group.

$X_5$ is preferably N, C—H or C—$OCH_3$;

$R_3{}^e$ is preferably hydrogen.

$R_4{}^e$ is preferably hydrogen or halo, such as iodo.

Suitable examples of $X_6$-$X_7$ when $CR_1{}^fR_2{}^f$-$CR_3{}^fR_4{}^f$ include $CH_2$—$CH_2$ CH=CH. $X_6$-$X_7$ is preferably $NR_z$—CO, however, such as NH—CO or NEt-CO.

$R_a{}^f$ is preferably hydrogen.

$R_b{}^f$ is preferably hydrogen or halo, such as iodo. Values for A include —$CH_2$—$(CH_2)_r$—$CH_2$— wherein r is 0, 1 or 2; —$CH_2$—CH=CH—; —C($CH_3$)=CH— or when $X^g$ is CH or N, A may be —$(CH_2)_2$—CH= or —CH=CH—CH=. Other examples of A are as described in the examples hereinafter.

$R_1{}^g$ and $R_2{}^g$ are often hydrogen or $R_1{}^g$ and $R_2{}^g$ are gem-dimethyl.

r is often 1.

$R_3{}^g$ is preferably hydrogen.

$R_4{}^g$ is preferably hydrogen or halo, such as fluoro.

Other suitable values of X are as described in PCT/GB93/020208, PCT/EP93/02808, PCT/EP93/02775, PCT/EP93/02809, PCT/GB93/02130 (all in the name of SmithKline Beecham plc).

Y is preferably O or NH.

$n^1$ is preferably 1 and the azacycle is preferably attached at a 4-position carbon atom, when q is 2.

Values of Z of interest include 4-piperidinylmethyl and 4-pyrrolidinylmethyl, N-substituted by $R_a$.

Values for $R_7$ when monocyclic heteroaryl include pyridyl, pyrimidyl, pyrazinyl, pyrryl, imidazolyl, thienyl, furanyl, oxazole or thiazole (all possible isomers). Bicyclic heteroaryl $R_7$ include benzofuranyl, benzothiophenyl, indolyl and indazolyl, quinolyl and isoquinolyl (all possible isomers).

Values for $R_7$ when 3 to 8 membered heterocyclyl, include cyclic polymethylene interrupted by one or two of N, O, or S, linked through C or N, for example N-linked piperidinyl or pyrrolidinyl.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

Examples of pharmaceutically acceptable salts include quaternary derivatives of the compounds of formula (I) such as the compounds quaternised by compounds $R_x$—T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples of T include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

The compounds of formula (I) wherein CO—Y is an ester or amide linkage are prepared by conventional coupling of the Z moiety with the appropriate acid. Suitable methods are as described in GB 2125398A (Sandoz Limited), GB 1593146A, EP-A-36269, EP-A-289170 and WO 92/05174 (Beecham Group p.l.c.). When CO—Y is replaced by a heterocyclic bioisostere, suitable methods are described in EP-A-328200 (Merck Sharp & Dohme Limited). Reference is also made to EP-A-501322 (Glaxo Group Limited).

The invention also comprises a process for preparing the compounds of formula (I) wherein X is of formula (d,), which comprises reacting an appropriate benzoic acid derivative with an appropriate alcohol or amine. A process comprises reacting a benzoic acid derivative wherein the aromatic substituents are as required in the end compound of formula (I), or substituents convertible thereto, with an alcohol or amine containing Z or a group convertible thereto, and thereafter if necessary, converting the benzoic acid substituents and/or Z, and optionally forming a pharmaceutically acceptable salt.

Suitable examples of conversions in the aromatic substituents include chlorination of hydrogen to chloro, reduction of nitro to amino, dehydrohalogenation such as debromination, and/or elaboration of a 2,3-disubstituted benzoic acid with ethylene glycol to form the benzodioxan. Any elaboration of X is, however, usually carried out prior to ester or amide coupling.

Suitable examples of conversions in the Z containing moiety include conventional modifications of the N-substituent by substitution and/or deprotection or, in the case of a 2-, 3- or 4- substituted piperidinyl desired end compound, reduction of an appropriate pyridyl derivative.

Values for Z containing intermediates are as described in the aforementioned patent publications in the name of SmithKline Beecham plc.

The compounds of the present invention are 5-HT$_4$ receptor antagonists and it is thus believed may generally be used in the treatment or prophylaxis of gastrointestinal disorders, cardiovascular disorders and CNS disorders.

They are of potential interest in the treatment of irritable bowel syndrome (IBS), in particular the diarrhoea aspects of IBS, i.e., these compounds block the ability of 5-HT to stimulate gut motility via activation of enteric neurones. In animal models of IBS, this can be conveniently measured as a reduction of the rate of defaecation. They are also of potential use in the treatment of urinary incontinence which is often associated with IBS.

They may also be of potential use in other gastrointestinal disorders, such as those associated with upper gut motility, and as antiemetics. In particular, they are of potential use in the treatment of the nausea and gastric symptoms of gastrooesophageal reflux disease and dyspepsia. Antiemetic activity is determined in known animal models of cytotoxicagent/radiation induced emesis.

Specific cardiac 5-HT$_4$ receptor antagonists which prevent atrial fibrillation and other atrial arrhythmias associated with 5-HT, would also be expected to reduce occurrence of stroke (see A. J. Kaumann 1990, Naumyn-Schmiedeberg's Arch. Pharmacol. 342, 619–622, for appropriate animal test method).

Anxiolytic activity is likely to be effected via the hippocampus (Dumuis et al 1988, Mol Pharmacol., 34, 820–887). Activity can be demonstrated in standard animal models, the social interaction test and the X-maze test.

Migraine sufferers often undergo situations of anxiety and emotional stress that precede the appearance of headache (Sachs, 1925, Migraine, Pan Books, London). It has also been observed that during and within 48 hours of a migraine attack, cyclic AMP levels are considerably increased in the cerebrospinal fluid (Welch et al., 1976, Headache 16, 160–167). It is believed that a migraine, including the prodomal phase and the associated increased levels of cyclic AMP are related to stimulation of 5-HT$_4$ receptors, and hence that administration of a 5-HT$_4$ antagonist is of potential benefit in relieving a migraine attack.

Other CNS disorders of interest include schizophrenia, Parkinson's disease and Huntingdon's chorea.

The invention also provides a pharmaceutical composition comprising a compound of formula (I), or a pharmaceutically acceptable salt thereof, and a pharmaceutically acceptable carrier.

Such compositions are prepared by admixture and are usually adapted for enteral such as oral, nasal or rectal, or parenteral administration, and as such may be in the form of tablets, capsules, oral liquid preparations, powders, granules, lozenges, reconstitutable powders, nasal sprays, suppositories, injectable and infusable solutions or suspensions. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of irritable bowel syndrome, dyspepsia, atrial arrhythmias and stroke, anxiety and/or migraine in mammals, such as humans, which comprises the administration of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 1000 mg for example 0.5 to 500 mg, of the compound of the invention. Unit doses may be administered once or more than once a day, for example, 2, 3 or 4 times a day, more usually 1 to 3 times a day, that is in the range of approximately 0.0001 to 50 mg/kg/day, more usually 0.0002 to 25 mg/kg/day.

No adverse toxicological effects are indicated within the aforementioned dosage ranges.

The invention also provides a compound of formula (I) or a pharmaceutically acceptable salt thereof for use as an active therapeutic substance, in particular for use in the treatment of irritable bowel syndrome, gastro-oesophageal reflux disease, dyspepsia, atrial arrhythmias and stroke, anxiety and/or migraine.

The following Examples illustrates the preparation of compounds of formula (I), and the following Descriptions relate to the preparation of intermediates. The compounds of formula (I-1) and intermediates are prepared in Examples and Descriptions 1-1, 2-1 etc, the compounds of formula (I-2) are prepared in Examples and Descriptions 1-2, 2-2 etc and similarly for the compounds of formulae (I-3) to (I-5).

It will be appreciated that any compound prepared wherein Y is O may be provided as the corresponding compound wherein Y is NH.

A preferred compound corresponds to any of the compounds prepared in the Examples, but wherein there is an amino substituent in the 4-position and a chloro substituent in the 5-position of the benzoic acid nucleus depicted in formulae (I-1) to (I-5) inclusive.

EXAMPLE 1

[X=(d), $X_1$—$(CH_2)_x$—$X_2$=O—$(CH_2)_2$—O, $R_1^d$=NH$_2$, $R_2^d$=Cl, $R_3^d$=H, $R_4^d$, $R_5^d$=H; Y=O, Z=4-piperidinylmethyl, $R_a$=3-pyridylmethyl]

5-(1-(3-Pyridylmethyl)-4-piperidinyl)methyl-8-amino-7-chloro-1,4-benzodioxancarboxylate (E1)

A stirred solution of 8-amino-7-chloro-1,4-benzodioxan-5-(4-piperidinylmethyl) carboxylate (0.1 g, 0.31 mmol) in acetone (10 ml) was treated with Et$_3$N (0.043 ml, 0.31 mmol) and 3-picolyl chloride (0.043 g, 0.34 mmol). The reaction mixture was heated under reflux for 48 hours, cooled and evaporated in vacuo. The oily residue was purified by silica gel chromatography using CHCl$_3$ increasing to 2% MeOH, 98%CHCl$_3$ as eluant to yield the title compound as a pale yellow gum (0.05 g) which was converted to the oxalate salt, mp 219°–221° C.

$^1$H NMR 250 MHz (CDCl$_3$) (free base)

δ:8.60–8.40(m,2H), 7.65(d,1H), 7.50(s,1H), 7.30–7.20 (m,1H), 4.45(s,2H), 4.40–4.25(m,4H), 4.10(d,2H),3.50(s, 2H), 2.90(d,2H), 2.00(t,2H), 1.75(d,2H), 1.50–1.25(m,3H)

EXAMPLE 2

[X=(g), X$^g$=O, A=(CH$_2$)$_3$, ($R_1^g$, $R_2^g$, $R_3^g$, $R_4^g$=H; Y=NH, Z=4-piperidinylmethyl, $R_a$=4-pyridylmethyl]

N-[(1-(4-Pyridylmethyl)-4-piperidinyl)methyl]3,4-dihydro-2H-[1,3]oxazino[3,2-a]indole-10-carboxamide (E2)

The title compound was prepared as an off-white solid by treating a solution of N-(4-piperidinylmethyl) 3,4-dihydro-2H-[1,3]oxazino[3,2-a]indole-10-carboxamide (D2) and triethylamine in acetonitrile and N,N-dimethylformamide with 4-picolyl chloride using the procedure described in Example 1.

$^1$H NMR (CDCl$_3$)

δ:8.55(d,2H), 8.35(d,1H), 7.10–7.40(m,5H), 6.57(t,1H), 4.55(t,2H), 4.14(t,2H), 3.51(s,2H), 3.37(t,2H), 2.80–2.98 (bd,2H), 2.30–2.50(m,2H), 1.93–2.14(m,2H), 1.50–1.93(m, 3H), 1.31–1.50(m,2H).

EXAMPLE 3

[X=(g), X$^g$=O, A=(CH$_2$)$_3$, ($R_1^g$,$R_2^g$,$R_3^g$,$R_4^g$=H; Y=NH, Z=4-piperidinylmethyl, $R_a$=2-(1-piperidinyl)ethyl]

N-[(1-(2-(1-Piperidinyl)ethyl-4-piperidinyl)methyl]3,4-dihydro-2H-[1,3]oxazino[3,2-a]indole-10-carboxamide (E3)

The title compound was prepared as an off-white solid by treating a solution of N-(4-piperidinylmethyl)3,4-dihydro- 2H-[1,3]oxazino[3,2-a]indole-10-carboxamide (D2) and triethylamine in acetonitrile and N,N-dimethylformamide with 1-(2-chloroethyl)piperidine using the procedure described in Example 1; mp 139°–141° C.

$^1$H NMR (CDCl$_3$)

δ:8.35(d,1H), 7.07–7.48(m,3H), 6.55(t,1H), 4.56(t,2H), 4.13(t,2H), 3.35(t,2H), 2.90–3.07(bd,2H, 2.28–2.60(m, 10H), 1.95–2.19(bt,2H), 1.23–1.90(m,11H).

EXAMPLE 4

[X=(g), X$^g$=O, A=(CH$_2$)$_3$, (R$_1^g$,R$_2^g$,R$_3^g$,R$_4^g$=H; Y=NH,Z=4-piperidinylmethyl, R$_1$=benzofuran-2-ylmethyl]

N-[(1-(Benzofuran-2-ylmethyl)-4-piperidinyl)methyl]3,4-dihydro-2H-[1,3]oxazino[3,2-a]indole-10-carboxamide (E4)

The title compound was prepared as an off-white solid by treating a solution of N-(4-piperidinylmethyl)3,4-dihydro-2H-[1,3]oxazino[3,2-a]indole-10-carboxamide (D2) and triethylamine in acetonitrile and N,N-dimethylformamide with 2-(chloromethyl)benzofuran (Blicke et al, J. Amer. Chem. Soc., 1949, 71, 2856) using the procedure described in Example 1.

$^1$H NMR (CDCl$_3$)

δ:8.32(d,1H), 7.40–7.62(m,2H), 7.02–7.37(m,5H), 6.61 (s,1H), 6.55(t,1H), 4.49(t,2H), 4.06(t,2H), 3.73(s,2H), 3.35 (t,2H), 2.95–3.15(bd,2H), 2.25–2.46(m,2H), 2.02–2.25(bt, 2H), 1.33–1.90(m,5H).

EXAMPLE 5

[X=(g), X$^g$=O, A=(CH$_2$)$_3$, (R$_1^g$,R$_2^g$,R$_3^g$,R$_4^g$=H: Y=NH, Z=4-piperidinylmethyl, R$_a$=quinolin-2-ylmethyl)]

N-[(1-(Quinolin-2-ylmethyl)4-piperidinyl)methyl]3,4-dihydro-2H-[1,3]oxazino[3,2-a]indole-10-carboxamide (E5)

The rifle compound was prepared by treating a solution of N-(4-piperidinylmethyl)3,4-dihydro-2H-[1,3]oxazino[3,2-a]indole-10-carboxamide (D2) and triethylamine in acetonitrile and N,N-dimethylformamide with 2-(chloromethyl)quinoline using the procedure described in Example 1.

$^1$H NMR (CDCl$_3$)

δ:8.32(d,1H), 8.16(d,1H), 8.08(d,1H), 7.65–7.90(m,3H), 7.54(t,1H), 7.07–7.35(m,3H), 6.58(t,1H), 4.52(t,2H), 4.09(t, 2H), 3.96(s,2H), 3.35(t,2H), 3.00–3.15(m,2H), 2.25–2.50 (m,4H), 1.35–1.95(m,5H).

EXAMPLE 6

[X=(g), X$^g$=O, A=(CH$_2$)$_3$, (R$_1^g$,R$_2^g$,R$_3^g$,R$_4^g$=H; Y=NH, Z=4-piperidinylmethyl, R$_a$=5-phenylpentyl]

N-[(1-(5-Phenylpentyl)-4-piperidinyl)methyl]3,4-dihydro-2H-[1,3]oxazino[3,2-a]indole-10-carboxamide (E6)

The title compound was prepared by treating a solution of N-(4-piperidinylmethyl)3,4-dihydro-2H-[1,3]oxazino[3,2-a]indole-10-carboxamide (D2) and triethylamine in acetonitrile and N,N-dimethylformamide with 1-chloro-5-phenylpentane using the procedure described in Example 1.

$^1$H NMR (CDCl$_3$)

δ:8.28(d,1H), 7.08–7.30(m,8H), 6.61(t,1H), 4.54(t,2H), 4.10(t,2H), 3.34(t,2H), 3.15–3.27(bd,2H), 2.52–2.66(m,4H), 2.26–2.43(m,4H), 1.55–1.97(m,9H), 1.26–1.42(m,2H).

EXAMPLE 7

[X=(g), X$^g$=O, A=(CH$_2$)$_4$, (R$_1^g$,R$_2^g$,R$_3^g$,R$_4^g$=H; Y=NH, Z=4-piperidinylmethyl, R$_a$=2-thienylmethyl]

N-[(1-(2-Thienylmethyl)-4-piperidinyl)methyl]3,4-dihydro-2H-[1,3]oxazino[3,2a]indole-10-carboxamide (E7)

The title compound was prepared by treating a solution of N-(4-piperidinylmethyl)3,4-dihydro-2H-[1,3]oxazino[3,2-a]indole-10-carboxamide (D2) and triethylamine in acetonitrile and N,N-dimethylformamide with 2-(chloromethyl) thiophene using the procedure described in Example 1.

$^1$H NMR(CDCl$_3$)

δ:8.32(d,1H), 6.85–7.35(m,6H), 6.55(bt,1H), 4.52(t,2H), 4.10(t,2H), 3.74(s,2H), 3.32(t,2H), 2.90–3.05(m,2H), 2.25–2.50(m,4H), 1.30–1.90(m,5H).

EXAMPLE 8

[X=(g), X$^g$=O, A=(CH$_2$)$_4$, (R$_1^g$,R$_2^g$,R$_3^g$,R$_4^g$=H; Y=NH, Z=4-piperidinylmethyl, R$_a$=2-cyclohexyl) ethyl]

N-[(1-(2-(Cyclohexyl)ethyl-4-piperidinyl)methyl]3,4-dihydro-2H-[1,3]oxazino[3,2-a]indole-10-carboxamide (E8)

The title compound was prepared by treating a solution of N-(4-piperidinylmethyl)3,4-dihydro-2H-[1,3]oxazino[3,2-a]indole-10-carboxamide (D2) and triethylamine in acetonitrile and N,N-dimethylformamide with 2-cyclohexylethyl bromide using the procedure described in Example 1.

$^1$H NMR(CDCl$_3$)

δ:8.28(d,1H), 7.10–7.35(m,3H), 6.64(t,1H), 4.57(t,2H), 4.13(t,2H), 3.22–3.44(m,4H), 2.65–2.80(m,2H), 2.30–2.55 (m,4H), 1.55–2.05(m,12H), 1.10–1.35(m,4H), 0.85–1.05(m, 2H).

EXAMPLE 9

[X=(g), X$^g$=O, A=(CH$_2$)$_4$, (R$_1^g$,R$_2^g$,R$_3^g$,R$_4^g$=H; Y=NH, Z=4-piperidinylmethyl, R$_a$=1-naphthylmethyl]

N-[(1-(1-Naphthylmethyl)-4-piperidinyl)methyl]3,4-dihydro-2H-[1,3]oxazino[3,2-a]indole-10-carboxamide (E9)

The title compound was prepared by treating a solution of N-(4-piperidinylmethyl)3,4-dihydro-2H-[1,3]oxazino[3,2-a]indole-10-carboxamide (D2) and triethylamine in acetonitrile and N,N-dimethylformamide with 1-bromomethylnaphthylene using the procedure described in Example 1.

$^1$H NMR (CDCl$_3$)

δ:8.23–8.48(m,2H), 7.70–7.90(m,2H), 7.33–7.57(m,4H), 7.00–7.30(m,3H), 6.52(t,1H), 4.46(t,2H), 4.01(t,2H), 3.90(s, 2H), 3.31(t,2H), 2.90–3.07(bd,2H), 2.22–2.40(m,2H), 2.07 (bt,2H), 1.55–1.85(m,3H), 1.20–1.50(m,2H).

EXAMPLE 10

[X=(d), X$_1$—CH$_2$)$_x$—X$_2$=O—(CH$_2$)$_2$—O, R$_1^d$=NH$_2$, R$_2^d$=Cl, R$_3^d$=H, R$_4^d$, R$_5^d$=H; Y=O, Z=4-piperidinylmethyl, R$_a$=2-carboethoxyethyl]

[1-(2-Carboethoxyethyl)-4-piperidinyl]methyl-8-amino-7-chloro-1,4-benzodioxan-5-carboxylate (E10)

4-Piperidinylmethyl-8-amino-7-chloro-1,4-benzodioxan-5-carboxylate (0.100 g; 0.31 mmol) was dissolved in acetone (10 ml) and treated with ethyl acrylate (0.037 ml, 0.34 mmol). The solution was heated at reflux (18 hours), cooled and evaporated in vacuo to a dark brown gum. The gum was purified by flash silica gel chromatography with $CHCl_3 \rightarrow 2\%$ $MeOH/CHCl_3$ as eluant to yield the title compound as a colourless oil (0.053 g; 41%) which was covered to the oxalate salt, mp=176°–178° C.

$^1$H NMR (270MHz, $CD_3OD$) (oxalate salt)

δ:7.40(s,1H), 4.27(s,2H), 4.20–4.10(m,2H), 3.60–3.50(d, 2H), 3.37(t,2H), 3.27–3.23(m,6H), 3.10–2.90(t,2H), 2.85(t, 2H), 2.10–1.90(d,2H), 1.70–1.55(m,1H), 1.30–1.20(m,3H)

EXAMPLE 11

[X=(d), $X_1$—$(CH_2)_x$—$X_2$=O—$(CH_2)_2$—O, $R_1{}^d$=$NH_2$, $R_2{}^d$=Cl, $R_3{}^d$=H, $R_4{}^d$, $R_5{}^d$=H; Y=O, Z=4-piperidinylmethyl, $R_1$=3-hydroxybutyl]

[1-(3-Hydroxybutyl)-4-piperidinyl]methyl-8-amino-7-chloro-1,4,benzodioxan-5-carboxylate (E11)

a) 4-Piperidinylmethyl 8-amino-7-chloro-1,4-benzodioxan-5-carboxylate (0.100 g; 10.31 mmol) was dissolved in acetone (10 ml and treated with triethylamine (0.043 ml; 0.31 mmol) and methyl vinyl ketone (0.026 ml; 0.34 mmol). The solution was heated at reflux (18 hours), cooled and evaporated in vacuo to a yellow gum. The gum was purified by flash silica-gel chromatography with $CHCl_3$ as eluant to yield [1-(3-oxobutyl)-4-piperidinyl]methyl 8-amino-7-chloro-1,4-benzodioxan-5-carboxylate as a colourless gum (0.050 g; 41%) which was converted to the oxalate salt.

m.p. 160° C. (Dec)

$^1$H NMR (250 MHz, $CDCl_3$) (Free base)

δ:7.47(s,1H), 4.47(s,2H), 4.40–4.30(m,4H), 4.10(d,2H), 2.90(d,2H), 2.65(s,4H), 2.17(s,3H), 2.00(t,2H), 1.85–1.70 (m,2H), 1.47–1.25(m,3H)

b) [1-(3-oxobutyl)-4-piperidinyl]methyl-8-amino-7-chloro-1,4,benzodioxan-5-carboxylate (0.135 g, 0.340 mmol) (was dissolved in EtOH (8 ml) and treated with $NaBH_4$ (0.013 g, 0.340 mmol) with stirring. After 1 h, the reaction mixture was evaporated under reduced pressure and the residue partitioned between $CH_2Cl_2$ and water. The aqueous layer was then extracted with $CH_2Cl_2$, and the combined organic layers were dried ($Na_2SO_4$) and evaporated under reduced pressure to give a colourless oil, which was purified by silica-gel chromatography ($CH_2Cl_2/10\%$ MeOH as eluant) to give the title compound as a colourless oil (0.048 g, 35%), which was converted to its oxalate salt m.p. 220°–220° C.

$^1$HNMR (200 MHz, $CDCl_3$) (free base) δ7.50(s,1H), 4.50(s,2H), 4.35(s,4H), 4.10(d,2H), 3.96(m,1H), 3.25(d, 1H), 3.00(d,1H), 2.65(m,2H), 2.18(t,1H), 2.00–1.35(m,9H), 1.20(d,3H).

DESCRIPTIONS

Description 1

(1-Benzyl-4-piperidinyl)methylamine(D1)

A stirred solution of isonipecotamide (30.1 g, 0.23 mole) and benzyl bromide (27.9 ml, 0.23 mole) in ethanol (250 ml) was treated with anhydrous potassium carbonate (64.9 g, 0.47 mole) and heated under reflux for 3 h. The mixture was allowed to cool, then filtered and the filtrate concentrated under vacuum. The residual oil was dissolved in chloroform (200 ml) and washed with water (1×150 ml), then dried ($Na_2SO_4$) and concentrated under vacuum to leave a yellow solid (41.0 g). This solid was mixed thoroughly with phosphorus pentoxide (38.3 g, 0.27 mole) and the mixture heated at 180° C. under nitrogen for 2.5 h with gentle stirring. The reaction mixture was allowed to cool, then treated with water (300 ml). When the solid mass had dissolved, the solution was basified by addition of solid $K_2CO_3$ and extracted with ethyl acetate (2×250 ml). The combined extracts were dried ($Na_2SO_4$) and concentrated in vacuo to leave a brown oil (35.3 g). This was dissolved in dry ether (250 ml) and added dropwise over 30 minutes to a stirred suspension of lithium aluminium hydride (10.1 g, 0.26 mole) in ether (150 ml) at 0° C. under nitrogen. When addition was complete, the mixture was allowed to warm up to room temperature and was stirred for 1.5 h. It was re-cooled to 0° C. and treated cautiously with water (10 ml), 10% NaOH solution (15 ml) and water again (25 ml). The mixture was filtered through kieselguhr and the filtrate concentrated in vacuo to leave a brown oil, which was distilled under vacuum to afford the title compound as a colourless oil after distillation (27.8 g, 67%) bp 106° C. at 0.25 mmHg.

$^1$H NMR ($CDCl_3$)

δ:7.20–7.37(m,5H), 3.48(s,2H), 2.85–2.95(m,2H), 2.55 (d,2H), 1.87–2.00(m,2H), 1.60–1.75(m,2H), 1.10–1.40(m, 5H).

Description 2 a) N-[(1-Benzyl-4-piperidinyl)methyl]indole-3-carboxamide

To a stirred solution of indole-3-carboxylic acid (15 g, 0.093 mole) in dichloromethane (250 ml) under nitrogen was added oxalyl chloride (8.7 ml, 0.10 mole) and dry dimethylformamide (6 drops). After 2 hours, the solvent was evaporated under reduced pressure. The residual acid chloride (0.093 mole) was dissolved in dichloromethane (100 ml) and added dropwise to a stirred solution of N-(1-benzyl-4-piperidinyl)methylamine (D1, 16.4 g, 0.093 mole) and triethylamine (15.5 ml, 0.11 mole) in dichloromethane (150 ml) at 5° C. After stirring at ambient temperature overnight, the reaction mixture was washed with 10% $Na_2CO_3$ and the organic phase was dried ($Na_2SO_4$). The solvent was evaporated under reduced pressure and the residual solid recrystallised from ethyl acetate to afford the title compound as a white solid (17.5 g, 60%).

$^1$H NMR ($CDCl_3$)

δ:9.90(s,1H), 7.85–7.95(m,1H), 7.64(d,1H), 7.15–7.43 (m,8H), 6.17(t,1H), 3.48(s,2H), 3.37(t,2H), 2.83–2.98(m, 2H), 1.87–2.08(m,2H), 1.54–1.82(m,3H), 1.23–1.50(m,2H).

b) N-[(1-Benzyl-4-piperidinyl)methyl]3,4-dihydro-2H-[1,3]oxazino[3,2-a]indole-10-carboxamide A stirred suspension of N-[(1-benzyl-4-piperidinyl) methyl]indole-3-carboxamide (17.5 g, 0.050 mole) in chloroform (250 ml) was treated with 3-bromo-1-propanol (10.1 ml, 0.11 mole) and N-chlorosuccinimide (8.7 g, 0.065 mole) at room temperature and a clear solution was obtained in 15 minutes. After 1 h the reaction mixture darkened in colour from pale yellow to orange and temperature rose to 38° C. After a further 1 h the reaction mixture was treated with 10% $NaHCO_3$ solution and the chloroform layer separated, dried ($Na_2SO_4$) and concentrated in vacuo to leave a yellow oil, which was chromatographed on silica gel eluting with 3% methanol/chloroform. The 2-(3-bromopropoxy)indole intermediate was dissolved in acetone (400 ml), treated with anhydrous potassium carbonate (11 g, 0.08 mole) and stirred at room temperature for 20 h. The reaction mixture was concentrated in vacuo and the residue treated with water (200 ml) and extracted with chloroform (2×250 ml). The combined extracts were dried ($Na_2SO_4$), concentrated in vacuo and the residue chromatographed on silica gel eluting with 5% methanol/chloroform to afford the title compound as a pale yellow oil (3.1 g, 15%). This was converted to its oxalate salt and crystallised from acetone as a white solid mp 169°–170° C.

Free base:- $^1H$ NMR ($CDCl_3$) δ:8.32(d,1H), 7.05–7.38 (m,8H), 6.53(t,1H), 4.50(t,2H), 4.08(t,2H), 3.48(s,2H), 3.31 (t,2H), 2.83–2.97(m,2H), 2.27–2.41(m,2H), 1.54–2.06(m, 5H), 1.25–1.45(m,2H).

c) N-(4-Piperidinylmethyl)3,4-dihydro-2H-[1,3]oxazino[3,2-a]indole-10-carboxamide A stirred suspension of N-[(1-benzyl-4-piperidinyl)methyl]3,4-dihydro-2H-[1,3]oxazino[3,2-a]indole-10-carboxamide oxalate salt (2.25 g, 0.0046 mole) in ethanol (100 ml) and glacial acetic acid (4 ml) was hydrogenated over 10% Pd-C (0.8 g) at atmospheric pressure and 45° C. for 18 h. The mixture was filtered and the filtrate concentrated in vacuo. The majority of the product was in the solid which had been filtered off. This material was shaken with concentrated potassium carbonate solution (50 ml) and chloroform (50 ml) together with the residue from the filtrate. The mixture was filtered, the chloroform layer separated and dried ($Na_2SO_4$), then concentrated in vacuo to afford the title compound (D2) as a white solid (1.52 g, 100%). This was recrystallised from chloroform/60–80 petrol mp 139°–141° C.

$^1H$ NMR ($CDCl_3$)

δ:8.32(d,1H), 7.03–7.30(m,3H), 6.53(t,1H), 4.48(t,2H), 4.05(t,2H), 3.30(t,2H), 3.02–3.15(m,2H), 2.52–2.70(m,2H), 2.27–2.40(m,2H), 1.65–1.90(m,4H), 1.10–1.30(m,2H).

Description 3

4-Piperidinylmethyl 8-amino-7-chloro-1,4-benzodioxan-5-carboxylate hydrochloride a) To a stirred solution of 8-amino-7-chloro-1,4-benzodioxan-5-carboxylic acid (prepared from the corresponding 7-H acid (prepared as in GB 1571278) by chlorination of the protected form) (1.10 g) in acetonitrile was added biscarbonyldiimidazole (0.77 g). The reaction mixture was stirred at room temperature for 1.5 hours. The solvent was removed under reduced pressure to afford crude 8-amino-7-chloro-1,4-benzodioxan-5-imidazolide.

b) To a solution of N-tert-butoxycarbonyl-4-hydroxymethyl piperidine (0.25 g) in dry THF (10ml) was added methyllithium (1.5M in diethylether; 0.78 ml) at 0° C. under a nitrogen atmosphere. Stirring was continued at ambient temperature for 10 min. 8-Amino-7-chloro-1,4-benzodioxan-5-imidazolide (0.33 g) in THF (10 ml) was added to the reaction mixture and stirring continued for 2 hours. The reaction mixture was cooled to 0° C. and water was added. The solvent was removed under reduced pressure and the residue partitioned between chloroform and water. The organic phase was washed with water (3x), dried ($Na_2SO_4$) filtered and concentrated in vacuo. Flash chromatography on silica using chloroform and ethanol as eluant gave the title compound (0.26 g).

$^1H$ NMR 250 MHz ($CDCl_3$)

δ:7.47(s,1H), 4.49(s,2H), 4.36(s,4H), 4.08–4.22(m,4H), 2.64–2.80(m,2H), 1.84–2.01(m,1H), 1.70–1.83(m,2H), 1.46 (s,9H), 1.18–1.38(m,2H)

c) HCl(g) was bubbled into a cooled solution of 8-amino-7-chloro-(N-tert-butoxycarbonyl-4-piperidylmethyl)-1,4-benzodioxan-5-carboxylate (0.26 g) in dioxan (50 ml) for 25 min. The solvent was concentrated in vacuo and the residue triturated with $Et_2O$ to afford pure title compound (0.12 g).

mp 249°–251° C.

$^1H$ NMR 250 MHz (DMSO)

δ:8.99–9.10(m,1H), 8.59–8.78(m,1H), 7.29(s,1H), 5.73(s,2H), 4.25–4.34(s,4H), 4.03(d,2H), 3.20–3.42(m,2H), 2.75–2.97(m,2H), 1.76–2.06(m,3H), 1.48–1.57(m,2H)

5-$HT_4$ RECEPTOR ANTAGONIST ACTIVITY

1) Guinea Pig Colon

Male guinea-pigs, weighing 250–400 g are used. Longitudinal muscle-myenteric plexus preparations, approximately 3 cm long, are obtained from the distal colon region. These are suspended under a 0.5 g load in isolated tissue baths containing Krebs solution bubbled with 5% $CO_2$ in $O_2$ and maintained at 37° C. In all experiments, the Krebs solution also contains methiothepin $10^{-7}M$ and granisetron $10^{-6}M$ to block effects at 5-$HT_1$, 5-$HT_2$ and 5-$HT_3$ receptors.

After construction of a simple concentration-response curve with 5-HT, using 30 s contact times and a 15 min dosing cycle, a concentration of 5-HT is selected so as to obtain a contraction of the muscle approximately 40–70% maximum($10^{-9}M$ approx). The tissue is then alternately dosed every 15 min with this concentration of 5-HT and then with an approximately equi-effective concentration of the nicotine receptor stimulant, dimethylphenylpiperazinium (DMPP). After obtaining consistent responses to both 5-HT and DMPP, increasing concentrations of a putative 5-$HT_4$ receptor antagonist are then added to the bathing solution. The effects of this compound are then determined as a percentage reduction of the contractions evoked by 5-HT or by DMPP. From this data, $pIC_{50}$ values are determined, being defined as the -log concentration of antagonist which reduces the contraction by 50%. A compound which reduces the response to 5-HT but not to DMPP is believed to act as a 5-$HT_4$ receptor antagonist.

The compounds tested had a $pIC_{50}$ of >7, E1 had a $pIC_{50}$ of >9.

2) Rat Oesophagus

Rat oesophageal tunica muscularis mucosae is set up according to Baxter et. al. Naunyn-Schmiedeberg's Arch. Pharmacol., 343, 439–446 (1991). The inner smooth muscle robe of the muscularis mucosae is isolated and mounted for isometric tension recording in oxygenated (95% $O_2$/5% $CO_2$) Tyrodes solution at 37° C. All experiments are performed in pargyline pre-treated preparations (100 μM for 15 min followed by washout) and in the presence of cocaine (30 μM). Relaxant responses to 5-HT are obtained after pre-contracting the oesophagus tissue with carbachol (3 μM).

We claim:

1. A compound according to formula (I):

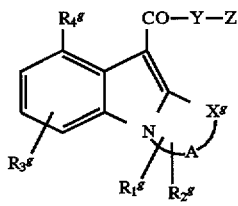

wherein $X^g$ is O, S, SO, $SO_2$, $CH_2$, CH, N or NR wherein R is hydrogen or $C_{1-6}$alkyl;

A is a saturated or unsaturated polymethylene chain of 2–4 carbon atoms;

$R_1{}^g$ and $R_2{}^g$ are hydrogen or $C_{1-6}$alkyl;
$R_3{}^g$ is hydrogen, halo, $C_{1-6}$alkyl, amino, nitro or $C_{1-6}$alkoxy;
$R_4{}^g$ is hydrogen, halo, $C_{1-6}$alkyl or $C_{1-6}$alkoxy;
Y is O or NH;
Z is of sub-formula:

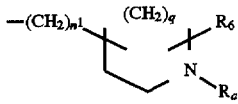

wherein
—$(CH_2)_n{}^1$ is attached at carbon; and
$n^1$ is 0, 1, 2, 3 or 4;
q is 0, 1, 2 or 3;
$R_a$ is a straight or branched chain alkylene of chain length 1–6 carbon atoms terminally substituted by $R_7$ wherein $R_7$ is 3 to 8 membered heterocyclyl, 5 or 6 membered monocyclic heteroaryl or 9 or 10 membered fused bicyclic heteroaryl linked through carbon, or $R_7$ is $C_{2-7}$alkoxycarbonyl or secondary or tertiary hydroxy substituted $C_{1-6}$alkyl; and
$R_6$ is hydrogen or $C_{1-6}$alkyl;
or a compound of formula (I) wherein the CO—Y linkage is replaced by a heterocyclic bioisostere.

2. A compound according to claim 1 wherein $n^1$ is 1, q is 2 and the azacycle is attached at a 4-position carbon atom.

3. A compound according to claim 1 wherein A is —$CH_2$—$(CH_2)_r$-$CH_2$—, wherein r is 0, 1 or 2; —$CH_2$—CH=CH=; or —$C(CH_3)$=CH—.

4. A compound according to claim 1 wherein $X^g$ is CH or N, and A is —$(CH_2)_2$—CH= or —CH=CH—CH=.

5. A compound according to claim 1 wherein Z is 4-piperidinylmethyl, N-substituted by $R_a$.

6. A compound according to claim 1 wherein Z is 4-pyrrolidinylmethyl, N-substituted by $R_a$.

7. A compound according to claim 1 wherein $R_{1g}$ and $R_2{}^g$ are both hydrogen or are gem-dimethyl.

8. A compound according to claim 1 wherein $R_4{}^g$ is hydrogen or halo.

9. A compound according to claim 1 wherein $R_7$ is pyridyl, pyrimidyl, pyrazinyl, pyrryl, imidazolyl, thienyl, furanyl, oxazole, thiazole, benzofuranyl, benzothiophenyl, indolyl, indazolyl, quinolyl and isoquinolyl.

10. A compound according to claim 1 wherein $R_7$ is piperidinyl or pyrrolidinyl.

11. A compound according to claim 1 which is: N-[(1-(4-pyridylmethyl)-4-piperidinyl)methyl]3,4-dihydro-2H-[1,3]oxazino[3,2-a]indole-10-carboxamide or a pharmaceutically acceptable salt thereof.

12. A compound according to claim 1 which is: N-[(1-(2-piperidinyl)ethyl)-4-piperidinyl)methyl]3,4-dihydro-2H-[1,3]oxazino[3,2-a]indole-10-carboxamide or a pharmaceutically acceptable salt thereof.

13. A compound according to claim 1 which is: N-[(1-(benzofuran-2-ylmethyl)-4-piperidinyl)methyl]3,4-dihydro-2H-[1,3]oxazino[3,2-a]indole-10-carboxamide or a pharmaceutically acceptable salt thereof.

14. A compound according to claim 1 which is: N-[(1-(quinolin-2-ylmethyl)-4-piperidinyl)methyl]3,4-dihydro-2H-[1,3]oxazino[3,2-a]indole- 10-carboxamide or a pharmaceutically acceptable salt thereof.

15. A compound according to claim 1 which is: N-[(1-(2-thienylmethyl)-4-piperidinyl)methyl]3,4-dihydro-2H-[1,3]oxazino[3,2-a]indole-10-carboxamide or a pharmaceutically acceptable salt thereof.

16. A pharmaceutical composition comprising a compound according to claim 1, and a pharmaceutically acceptable carrier.

17. A method for treating irritable bowel syndrome comprising administering an effective amount of a compound according to claim 1.

18. A method for treating atrial arrhythmia or stroke comprising administering an effective amount of a compound according to claim 1.

19. A method of treating anxiety comprising administering an effective amount of a compound according to claim 1.

20. A method of treating migraine comprising administering an effective amount of a compound according to claim 1.

21. A method of treating dyspepsia comprising administering an effective amount of a compound according to claim 1.

* * * * *